United States Patent
Quistgaard et al.

(10) Patent No.: US 8,337,407 B2
(45) Date of Patent: Dec. 25, 2012

(54) ARTICULATING ARM FOR MEDICAL PROCEDURES

(75) Inventors: Jens U. Quistgaard, Seattle, WA (US); Tim Etchells, Bothell, WA (US); Gregory Paul Darlington, Snohomoish, WA (US); Charles S. Desilets, Edmonds, WA (US)

(73) Assignee: LipoSonix, Inc., Hayward, CA (US)

( * ) Notice: Subject to any disclaimer, the term of this patent is extended or adjusted under 35 U.S.C. 154(b) by 1666 days.

(21) Appl. No.: 11/027,498

(22) Filed: Dec. 29, 2004

(65) Prior Publication Data
US 2005/0154295 A1    Jul. 14, 2005

Related U.S. Application Data

(63) Continuation-in-part of application No. 10/751,344, filed on Dec. 30, 2003.

(51) Int. Cl.
*A61B 8/00* (2006.01)
*A61N 7/00* (2006.01)

(52) U.S. Cl. .......................................... 600/439; 601/2
(58) Field of Classification Search .................. 600/424, 600/437, 414, 407, 439; 606/1, 130; 414/680; 601/2
See application file for complete search history.

(56) References Cited

U.S. PATENT DOCUMENTS

| | | | |
|---|---|---|---|
| 3,880,393 A | 4/1975 | Watson | |
| 4,002,221 A | 1/1977 | Buchalter | |
| 4,059,098 A | 11/1977 | Murdock | |
| 4,137,777 A | 2/1979 | Haverl et al. | |
| 4,211,949 A | 7/1980 | Brisken et al. | |
| 4,291,578 A | 9/1981 | Hetz et al. | |
| 4,326,418 A | 4/1982 | Pell, Jr. | |
| 4,368,410 A | 1/1983 | Hance et al. | |
| 4,437,033 A | 3/1984 | Diepers | |
| 4,459,854 A | 7/1984 | Richardson et al. | |
| 4,501,557 A | 2/1985 | Tamura et al. | |
| 4,552,151 A | 11/1985 | Bolomey et al. | |
| 4,556,066 A | 12/1985 | Semrow | |
| 4,567,895 A | 2/1986 | Putzke | |
| 4,593,699 A | 6/1986 | Poncy et al. | |

(Continued)

FOREIGN PATENT DOCUMENTS
GB    820814    9/1959

OTHER PUBLICATIONS

Ayme et al., "Occurance of Transient Cavitation in Pulsed Swatooth Ultrasonic Fields", *J. Acoust. Soc. Am.* (1988) 84(5):1598-1605.

(Continued)

*Primary Examiner* — Long V. Le
*Assistant Examiner* — Katherine Fernandez
(74) *Attorney, Agent, or Firm* — Wood, Herron & Evans, LLP

(57) ABSTRACT

A two-stage control system is disclosed being made of a first control means for providing command and control of a robotic arm, and a second control means for the control and movement of a therapy device, such as an ultrasound transducer. The therapy device is positioned within a therapy head. The therapy head is attached to the distal end of the robotic arm. The two-stage control system provides for a macro and micro level of control for the therapy device during a therapy procedure.

13 Claims, 14 Drawing Sheets

U.S. PATENT DOCUMENTS

| | | | |
|---|---|---|---|
| 4,854,808 A | 8/1989 | Bisiach | |
| 4,865,042 A | 9/1989 | Umemura et al. | |
| 4,901,073 A | 2/1990 | Kibrick | |
| 4,960,107 A | 10/1990 | Aida et al. | |
| 5,064,340 A | 11/1991 | Genov et al. | |
| 5,086,401 A * | 2/1992 | Glassman et al. | 700/259 |
| 5,102,280 A | 4/1992 | Poduje et al. | |
| 5,259,383 A | 11/1993 | Holstein et al. | |
| 5,301,660 A | 4/1994 | Rattner | |
| 5,308,222 A | 5/1994 | Bacchi et al. | |
| 5,352,301 A | 10/1994 | Panchanathan et al. | |
| 5,382,286 A | 1/1995 | Fanning et al. | |
| 5,382,885 A * | 1/1995 | Salcudean et al. | 318/568.11 |
| 5,404,387 A | 4/1995 | Hammond et al. | |
| 5,419,327 A | 5/1995 | Rohwedder et al. | |
| 5,434,208 A | 7/1995 | Batelaan et al. | |
| 5,476,438 A | 12/1995 | Edrich et al. | |
| 5,477,736 A | 12/1995 | Lorraine | |
| 5,505,206 A | 4/1996 | Walloch | |
| 5,526,815 A | 6/1996 | Granz et al. | |
| 5,568,810 A | 10/1996 | Hamers et al. | |
| 5,613,419 A | 3/1997 | Pierson et al. | |
| 5,623,928 A | 4/1997 | Wright et al. | |
| 5,626,554 A | 5/1997 | Ryaby et al. | |
| 5,669,150 A | 9/1997 | Guertin et al. | |
| 5,676,159 A | 10/1997 | Navis | |
| 5,695,500 A * | 12/1997 | Taylor et al. | 606/130 |
| 5,738,098 A | 4/1998 | Brock-Fisher et al. | |
| 5,738,635 A | 4/1998 | Chapelon et al. | |
| 5,755,753 A | 5/1998 | Knowlton | |
| 5,769,790 A | 6/1998 | Watkins et al. | |
| 5,807,377 A | 9/1998 | Madhani et al. | |
| 5,820,623 A | 10/1998 | Ng | |
| 5,852,413 A | 12/1998 | Bacchi et al. | |
| 5,871,446 A | 2/1999 | Wilk | |
| 5,938,608 A | 8/1999 | Bieger et al. | |
| 5,938,922 A | 8/1999 | Fulk, Jr. et al. | |
| 6,039,689 A | 3/2000 | Lizzi | |
| 6,039,694 A | 3/2000 | Larson et al. | |
| 6,085,749 A | 7/2000 | Wardle et al. | |
| 6,113,558 A | 9/2000 | Rosenschein et al. | |
| 6,126,619 A | 10/2000 | Peterson et al. | |
| 6,142,748 A | 11/2000 | Harris et al. | |
| 6,144,875 A * | 11/2000 | Schweikard et al. | 600/427 |
| 6,152,137 A | 11/2000 | Schwartz et al. | |
| 6,217,515 B1 | 4/2001 | Yamakawa et al. | |
| 6,233,476 B1 | 5/2001 | Strommer et al. | |
| 6,261,249 B1 | 7/2001 | Talish et al. | |
| 6,264,605 B1 | 7/2001 | Scirica et al. | |
| 6,302,848 B1 | 10/2001 | Larson et al. | |
| 6,306,146 B1 | 10/2001 | Dinkler | |
| 6,312,211 B2 | 11/2001 | Tranchida | |
| 6,366,831 B1 | 4/2002 | Raab | |
| 6,368,331 B1 | 4/2002 | Front et al. | |
| 6,419,648 B1 | 7/2002 | Vitek et al. | |
| 6,423,077 B2 | 7/2002 | Carol et al. | |
| 6,425,865 B1 * | 7/2002 | Salcudean et al. | 600/437 |
| 6,488,030 B1 | 12/2002 | Wardle et al. | |
| 6,488,639 B1 | 12/2002 | Ribault et al. | |
| 6,506,171 B1 | 1/2003 | Vitek et al. | |
| 6,507,309 B2 | 1/2003 | McMakin et al. | |
| 6,554,826 B1 | 4/2003 | Deardorff | |
| 6,561,389 B1 | 5/2003 | Earle | |
| 6,575,906 B1 | 6/2003 | Schembri, Jr. et al. | |
| 6,607,498 B2 | 8/2003 | Eshel | |
| 6,613,004 B1 | 9/2003 | Vitek et al. | |
| 6,618,620 B1 | 9/2003 | Freundlich et al. | |
| 6,846,290 B2 * | 1/2005 | Lizzi et al. | 600/439 |
| 2002/0016541 A1 * | 2/2002 | Glossop | 600/407 |
| 2002/0128592 A1 | 9/2002 | Eshel | |
| 2002/0193685 A1 * | 12/2002 | Mate et al. | 600/424 |
| 2003/0050654 A1 | 3/2003 | Whitman et al. | |
| 2003/0083536 A1 * | 5/2003 | Eshel et al. | 600/2 |
| 2004/0039312 A1 | 2/2004 | Hillstead et al. | |
| 2004/0128026 A1 * | 7/2004 | Harris et al. | 700/245 |

OTHER PUBLICATIONS

Clarke et al., "Physical and Chemical Aspects of Ultrasonic Disruption of Cells," *J. Acoust. Soc. Am.* (1970) 47(2):649-653.

Flynn et al., "A Mechanism for the Generation of Cavitation Maxima by Pulsed Ultrasound," *J. Acoust. Soc. Am.* (1984) 76(2):505-512.

Fry et al., "Threshold Ultrasonic Dosages for Structural Changes in the Mammalian Brain," *J. Acoust. Soc. Am.* (1970) 48(6):1413-1417.

Kinney, "Body Contouring with External Ultrasound," *Plastic & Reconstruct. Surg.* (1999) 103:728-729.

Padmaker, "Thresholds and Mechanisms of Ultrasonic Damage to 'organized' Animal Tissues *Symposium on Biological Effects and Characterizations of Ultrasound Sources*," (1977) Hazzard et al., Eds., pp. 224-239.

Romer Cimcore, "Infinite" [brochure], retrieved from the Internet: <<http://www.romer.com/main/index.php>> on Nov. 11, 2005, 1 page only.

* cited by examiner

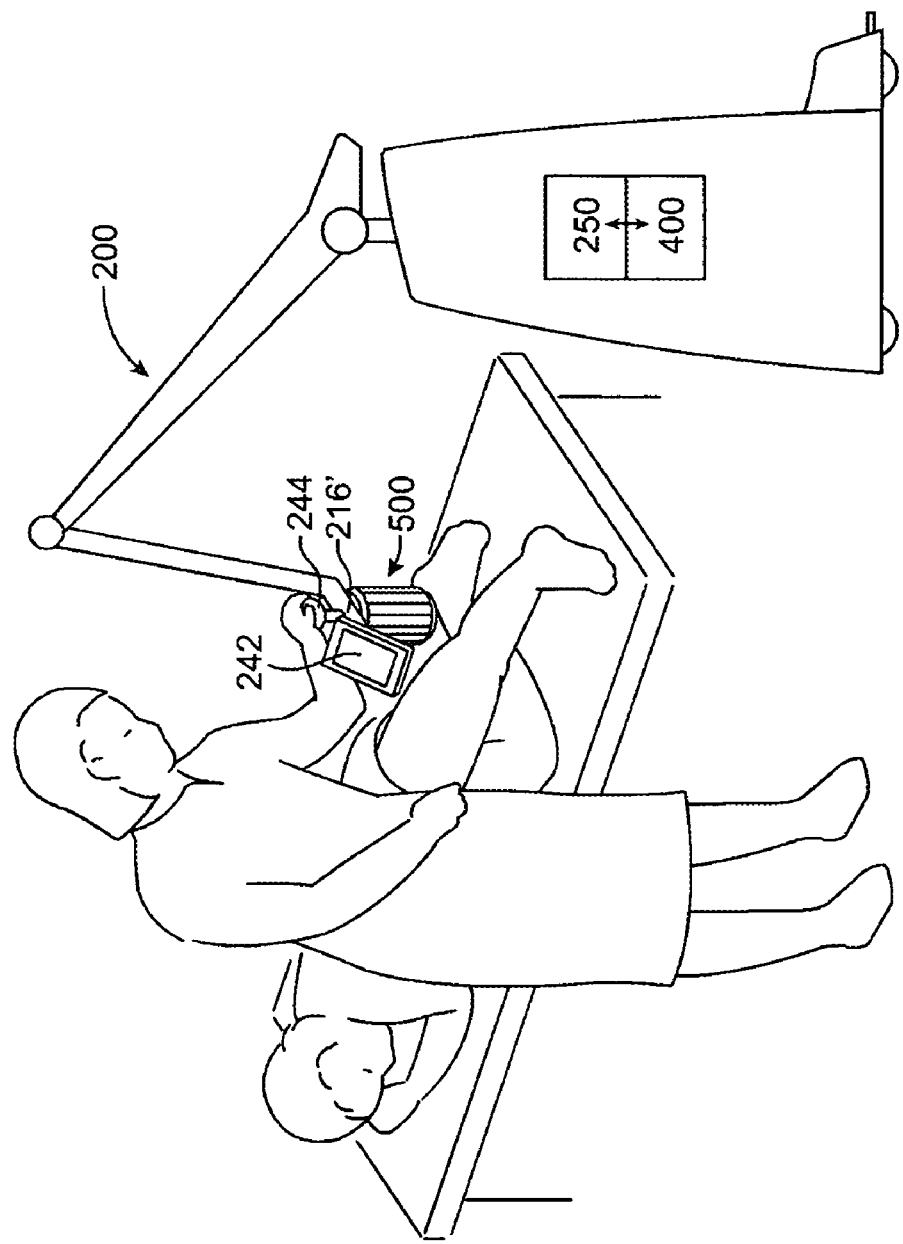

ARTICULATING ARM FOR MEDICAL PROCEDURES

CROSS-REFERENCES TO RELATED APPLICATIONS

The subject matter of the present application is a continuation-in-part of U.S. patent application Ser. No. 10/751,344, filed Dec. 30, 2003, entitled "Articulating Arm for Medical Procedures"; and related to the following application Ser. No. 11/026,519, filed on the same day as the present application, entitled "Systems and Methods for the Destruction of Adipose Tissue"; Ser. No. 10/750,370, entitled "Medical Device Inline Degasser"; Ser. No. 10/750,369, entitled "Disposable Transducer Seal"; 60/533,528, entitled "Position Tracking Device"; 60/533,988, entitled "Method for Planning and Performing Ultrasound Therapy"; 60/534,036, entitled "Ultrasound Therapy Head with Movement Control"; 60/533,958, entitled "Systems and Methods for the Destruction of Adipose Tissue"; 60/534,034, entitled "Component Ultrasound Transducer"; 60/630,857, entitled "Systems and methods for the destruction of adipose tissue"; the full disclosure of each of these applications are incorporated herein by reference.

BACKGROUND OF THE INVENTION

1. Field of the Invention

The present invention relates to a controller for use with an articulating arm used in non-invasive medical procedures.

2. Background of the Present Invention

Presently there are numerous methods and devices used by medical professionals to keep a medical device in close proximity to a patient during a procedure. These devices are largely deployed by hand, positioned by hand and rely on tension mechanisms to maintain their position relative to the patient.

Among the prior art, there are few articulating arms used in the medical industry for maintaining the precise location of an effector at the tip of an articulating arm to a patient. Articulating arms are used in various other industries such as manufacturing, machine tooling and robotic applications. Applications in manufacturing for heavy lifting and repetitive tasks may use robotic arms or load balancing arms. Robotic arms are capable of performing repetitive tasks and tasks involving heavy lifting so that a user is not burdened with performing these operations. Robotic arms are programmable so they can move autonomously between two or more positions. Generally a user programs the arm to move between a first position and any number of secondary positions so the robotic arm can carry out numerous tasks. Robotic arms are used on assembly lines to move parts from supply areas to assembly areas, and to secure parts to each other in assemblies, such as in the production of automobiles, circuit boards and other mass produced items. Robotic arms generally use encoders or other position sensors so the machine controlling the arm, be it a variable stage computer program or a simple electronic controller, know where the robotic arm is and how much it needs to be moved to perform its task. While robotic arms are enormously useful devices, they are primarily used in assembly and routine repetitive tasks. There are few robotic arms having the delicate and intricate movement ability as is demanded and required in medical procedures.

U.S. Pat. No. 4,291,578 describes an articulating arm for use with an ultrasound probe. The probe is used to guide an invasive insertion (needle or catheter) and the arm has a spring responsiveness giving it a light touch for easy use. The arm is attached to a vertical support extending from a pivoting and weighted base incorporated into a bed. The reach of the arm is restricted to the top half (torso) of the patient body.

U.S. Pat. No. 5,807,377 described an endoscopic robotic device for use in a minimally invasive surgical procedure. The manipulation of the medical device at the end of the manipulator arm is achieved by handles offering high dexterity and low friction. However such manipulator arms are not suited for carrying or maneuvering heavy objects.

U.S. Pat. No. 6,488,030 describes an apparatus for use in a medical biopsy procedure. An articulating arm is used having a stage or platform at the end that includes a micro-advancement control for ultra fine advancement of a biopsy probe. The arm is positioned manually in relation to the patient and the platform on the articulating arm is designed for use with a minimally invasive procedure.

U.S. application Ser. No. 10/751,344 describes an articulating arm in either a load balancing or powered robotic mode. The arm is used to maneuver a therapy device into position over a patient. The movement of the arm is guided either by direct manipulation of a human being, or by a computer. This application is herein incorporated by reference.

Various instruments designed for minimally invasive procedures also utilize robotic or semi-autonomous features. However these devices are not suited for noninvasive procedures.

Generally load balancing arms enable a user to grab and move loads directly in a natural manner. The weight of the load is compensated for so the user feels the load is within his or her natural lifting capacity. The load balancing arm provides the advantage of allowing a human user to guide the arm to move objects in a natural manner. That is to say, load balancing arms are designed primarily to assist a user in moving heavy objects by supplementing a person's lifting ability, and moving in the same motions a human being normally makes. The closer the load balancing arm lifting force is to the weight of the load, the less force the user is required to exert on the arm to move the load. Because load balancing arms are generally assisting devices that rely on a user to guide and control their movement, there is no need for any sort of position control or tracking of the movement of a load balancing arm. Some arms used for providing industrial measurement of solid objects provide limited forms of counter weighting and position encoders, however these devices are not designed for carrying any sort of substantial loads, nor do they provide for any form of adaptive positioning.

Thus there are no robotic arms or load balancing arms that provide a combination of; feather touch, location controller and location awareness in real time, and with the ability and design for use in a medical environment.

Thus there remains a need in the art for a device that can provide a full range of motion over a patient body, allowing a physician or user to place an effector at the end of an articulating arm, and to control its precise relational position with the patient, and control the position either manually or automatically.

There is also a need for a device that can provide adaptive positioning and match the regular movement of a patient body (e.g. breathing) so that the effector of the articulating arm does not change position relative to the patient during the course of the procedure unless specifically intended to do so by the physician.

There is further a need for an articulating arm for medical procedures having a load balancing mechanism for procedures of extended duration, or procedures requiring an effector to be properly positioned and provide a hands free environment for the user to do something else.

There is still further a need for a closed loop controller for the precise control of the effector in relationship to both the patient and the external environment. At least one of these needs is addressed by the following disclosure.

BRIEF SUMMARY OF THE INVENTION

The present invention provides a system for positioning a medical device. The system comprises a robotic arm with a first control means for controlling the robotic arm. There is a medical device movably positioned within a therapy head. The therapy head is connected to the robotic arm. There is a second control means for controlling the movement of the medical device within the therapy head. An electronic controller is in electronic communication with, and provides for the cooperative operation of, the robotic arm, the first control means, the medical device, and the second control means.

In an alternative embodiment there is a system that comprises a robotic arm with a control means for controlling the robotic arm. There is a medical device fixedly positioned within a therapy head. The therapy head is connected to the robotic arm. There is an electronic controller for translating the movement instructions received from the control means, and relaying the movement instructions to the robotic arm. An artificial wobble is added to the movement instructions to the robotic arm.

There is also described an apparatus for guiding the movement of an energy emitter over a patient body. The apparatus comprising a movable therapy head having at least one energy emitter, a guide ring, and a tracking system for following the movement of the guide ring and keeping the housing substantially centered within the guide ring.

In still another embodiment there is a system for positioning a medical device, the system comprising a load balancing arm, a medical device movably positioned within a therapy head, the therapy head being connected to the load balancing arm, and a means for controlling the movement of the medical device within the therapy head.

BRIEF DESCRIPTION OF THE DRAWINGS

FIG. 7A-C illustrates the motion range of the therapy head relative to a patient body.

DETAILED DESCRIPTION OF THE INVENTION

Figure 1:
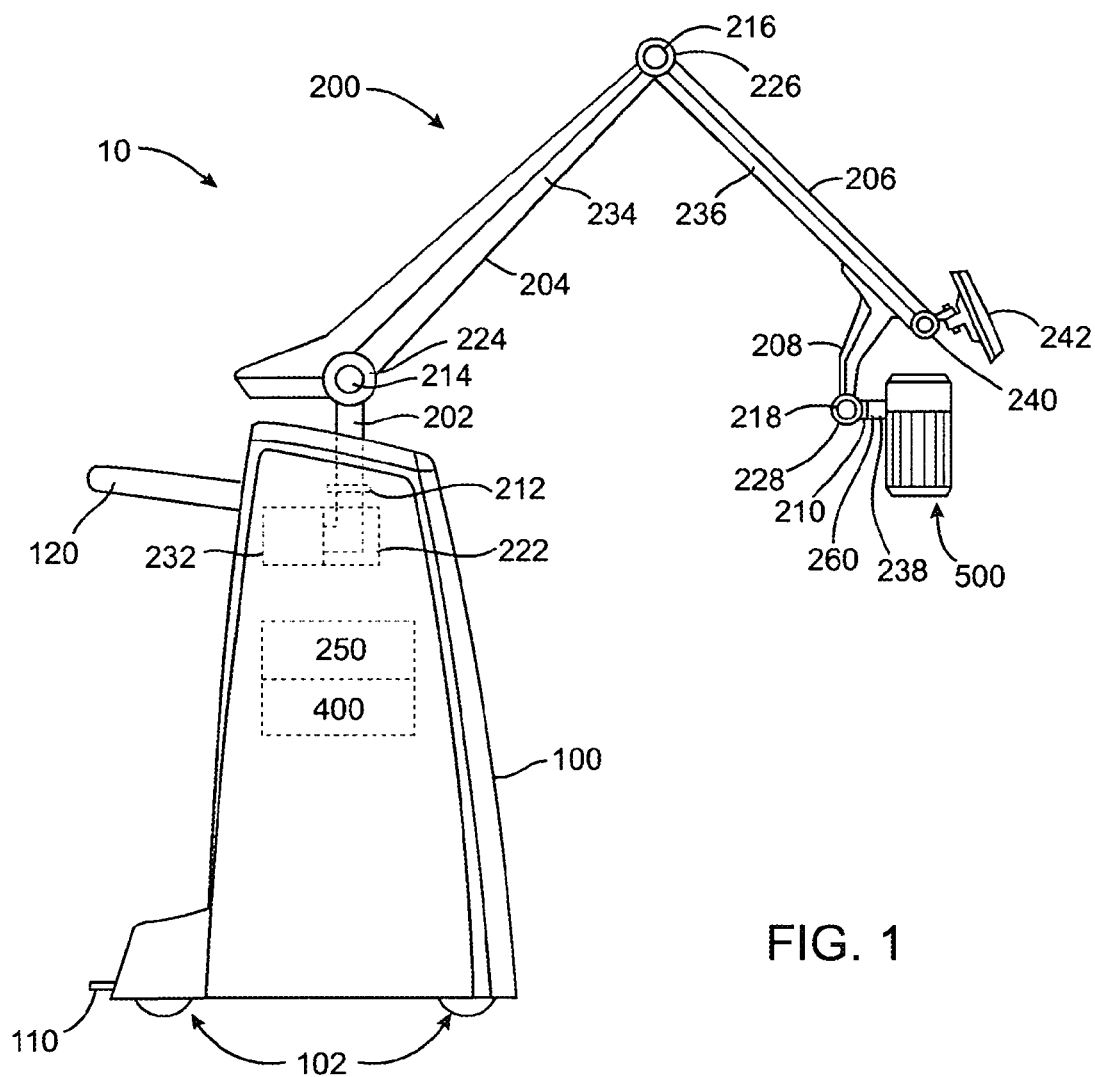
FIG. 1 shows an articulating arm of the prior art.

By "medical device" we mean a medical instrument such as an ultrasound transducer, therapy transducer or sensor device being positioned within a therapy head. The medical device may be a single instrument, or an assembly of instruments intended to interact as a single operable unit to perform a medical procedure. For example, a therapy ultrasound transducer coupled to either an A-line transducer or a diagnostic transducer to provide tissue imaging simultaneously with an ultrasound therapy procedure would form the medical device. Multiple devices operating cooperatively to perform a single medical procedure may form the medical device, though each of them may be operated individually in a non-cooperative form outside the scope of the present invention.

By "therapy head" we mean a housing for containing the medical device. The housing may be specially designed to be form fitted over the medical device minimizing the bulk of the housing, or a housing having additional volume for the incorporation of additional devices. Such devices may include a small motor system for moving the medical device within the housing, or the use of a fluid reservoir, or having additional sensors, guidance devices for relaying information to components positioned to the exterior of the therapy head. In previous descriptions we assign the term "end effector" or "effector" to the "therapy head." The use of the terms "therapy head", "effector", and "end effector" are considered interchangeable.

The various components of the system described herein are for the most part, electronic in nature. We use the phrase "electronic communication" herein to mean the electronic connection between various parts of the system or apparatus described herein, as well as the transfer or communication of data between the various components. So "electronic communication" herein means the relaying of data, commands, signals, and/or power.

The present apparatus relates to a system for guiding a medical device for a noninvasive medical procedure. In a principle embodiment, there is a system for positioning a medical device attached to a robotic arm. The system comprises a robotic arm and a first control means for controlling the robotic arm. The medical device is movably positioned within a therapy head. The therapy head is connected to the robotic arm. There is a second control means for controlling the movement of the medical device within the therapy head. There is an electronic controller in electronic communication with, and for the cooperative operation of; the robotic arm, the first control means, the medical device and the second control means.

In a second embodiment, there is a system for the positioning of a medical device, the system comprising a robotic arm and a control means for controlling the robotic arm. There is a medical device fixedly positioned within a therapy head with the therapy head being movably connected to the robotic arm. There is an electronic controller for translating the instructions received from the control means, and relaying the movement instructions to the robotic arm. An artificial wobble may be automatically introduced to the movement instructions to the robotic arm.

The robotic arm described herein has been previously described in parent U.S. application Ser. No. 10/751,344. The contents of which are herein incorporated by reference. The robotic arm is used to carry a therapy device and maintain the position of the therapy device relative to a patient body. The therapy head is potentially too heavy for a user to support the weight of it for the length of a medical procedure without the mechanical assistance of the robotic arm. A mechanical support is needed. The robotic arm has one or more force generating devices, such as motors, for moving a plurality of arm segments. The arm has multiple degrees of freedom allowing the therapy head to be positioned and moved as desired. Previously we describe the robotic arm as either having motors which allow for a user to guide the arm into position manually with a feather touch control, or for the arm to be of a load balancing type. In the present disclosure, we are concerned primarily with robotic arms, or balancing arms also having motor force capabilities to provide the equivalent of a light or "feather" touch.

The guidance system for the therapy device positioned on the robotic arm is preferably made of two components working cooperatively. The first control means provides a "macro" level of control to the therapy device, by controlling the movement of the robotic arm. The second control means provides a "micro" level of control to the medical device within the therapy head.

Command and control of the robotic arm is provided by a first control means. The first control means provides movement instructions to the motors or other force generating means of the robotic arm. In addition to movement instructions for the robotic arm, the first control means can also provide virtual position information to a user through a visual display.

The first control means may be a variety of different devices capable of guiding the movement of the robotic arm. In a first embodiment of the first control means, a computer input device can be used to provide both virtual positioning of the therapy head, and movement instructions to the robotic arm. The computer input device may be any of a class of input device normally used to provide movement commands to a pointer (cursor) on a computer screen. These are in general two dimensional input devices such as a mouse, tablet device or trackball. In addition three dimensional input devices can be used to provide virtual positioning in a three dimensional visual frame on a computer screen. Such devices are commonly exemplified in joysticks, D-controllers and the like. Finally true freedom on movement in a virtual environment can be provided by a six degree of freedom (DOF) device, such as a "spaceball" input device commonly used in Computer Aided Design (CAD) applications. The input device used as the first control means may be an off the shelf type of computer input device, or a specially designed device to operate with the robotic arm. The device used for the first control means may be interchangeable, so that depending on user preference or medical procedure requirements, a different input device may be used from one procedure to the next, even when using the same robotic arm.

Although it is preferable for the robotic arm and the input device to have the same DOF, it is not essential. The input device used for the first control means may be interchangeable. That is to say it is not necessary that the input device be either permanently or fixedly attached to the robotic arm. The input device may connect through a computer connection interface such as are commonly used for computer input devices. Thus one input device may have three DOF while another has six DOF, yet both are adaptable to command and control the robotic arm through a common interface port. Ideally the robotic arm has six DOF through the therapy head, and has sufficient mobility and extension to allow the six DOF to be conveyed to the therapy head without physically interfering with other objects present during a medical procedure, such as the patient or the user.

The movement of the input device produces movement instructions in the same way as a computer input device produces virtual location information for a cursor or other virtual object to be displayed on a computer screen. However in addition to the virtual movement and location information provided by the input device, the movement information is also translated into actual movement commands for the motors or force generating devices used to control the robotic arm. In this manner the use of a computer input device allows a user to manipulate a potentially heavy and cumbersome medical device with no more effort than is needed to operate a computer input device. Unlike some computer input devices that are of fixed orientation (such as I-beams or cursor arrows), the orientation of the cursor displayed on the computer screen for the input device described herein preferably corresponds to a known orientation of the medical device. For instance the cursor arrow may point in the same direction as the medical device emits energy, or in the opposite direction. Thus movement of the input device, and changes in the orientation of the cursor in a virtual environment will produce a corresponding change in the position and orientation of the medical device or therapy head.

Similar to a normal computer input device, the input device used with the system of the present invention may have buttons or scroll wheels or other actuators on them that may be programmed to correspond to particular operable elements of the system. For example the buttons on the input device may be used to toggle between turning the motor of the robotic arm on or off, activating the medical device either to perform a therapy treatment or refresh some sensor data.

An important distinction in the application of input devices to the present disclosure with the general application of such devices is the repositioning aspect of such input devices. It is perhaps common knowledge that a computer input device may be repositioned with ease to compensate for ergonomic desires of the user. For instance a mouse or joy stick may be picked up and moved while the virtual position of the mouse pointer, I-beam and the like remains the same. This advantage of the computer input device can be adapted to the input device used as a first control means for the robotic arm within certain limitations.

The advantage can be translated into control of the robotic arm where the movement of the therapy head, medical device or robotic arm is also suspended while the input device is being repositioned. However the advantage cannot be translated where the input device is being used to trace over a path that is either an actual placement of the therapy head, medical device or robotic arm in relation to the patient (see below) or a representative depiction of the position of the therapy head, medical device or robotic arm with respect to the patient body.

A representative placement involves either a map or a model of the patient skin surface to be used instead of the actual skin surface. In one alternative embodiment of the tracking system, a map can be created of the patient skin surface using a projection image and a camera. A projector casts an image on the patient body of regularly spaced gridlines, or grid squares. The lines are projected from a template, the template having a known line spacing. The line spacing may be regular or irregular so long as the distance between each line is known. The projected line image falls on the patient surface where it can be detected by a camera at an angle off the projection line. The camera reads the distances between the lines producing a second distance value for a side of a right triangle. Thus using simple trigonometry, the elevation distance between lines can be determined.

A tracking system can follow a two dimensional image of the projected map, wherein the actual distances on slope surfaces is determined by mathematical calculation rather than from direct measurement. In this manner the two dimensional map provides a good approximation of the distances and slopes and allows the ultrasound system to adapt to the longer (or shorter) slope distances and transmit the appropriate level of energy.

Similarly in another embodiment of the tracking system, a three dimensional representation of the patient can be used. The three dimensional representation can be a contoured dummy, or a cast derived from the body of the actual patient. The three dimensional need not be large or precise so long as it is large enough to encompass the desired treatment area, and accurate enough so that the focal zone of the transducer that will track over the actual patient body, does not project into muscle tissue or other tissue that should not be treated.

In either of these tracking system embodiments, it should be appreciated that it is both desirable and beneficial to maintain sufficient accuracy in the model or tracking system using a proxy for the patient skin surface, that the actual therapy device continues to treat only undesirable adipose tissue. A imaging or a-line scanning transducer can be used to ensure therapy is applied strictly to adipose tissue during a therapy session. This permits the detection of adipose tissue in real time, and provides a detection means for the system to be shut off, or shut down in the event the imaging sensor detects non-adipose tissue. Even if the user feels the therapy head is over the proper adipose tissue zone, the device itself has a safety back up.

In an actual placement situation, the repositioning of the input device would similarly be undesirable for the same reasons above, except the repositioning of the input device would correspond to a direct change in the placement of the medical device, therapy head or robotic arm.

The computer input device used as the first control means may be directly mounted on the robotic arm. Preferably an input device having six DOF would be mounted in this case, and located substantially near the therapy head. A user can operate the input device by manually manipulating the input device (such as a joystick or spaceball) and seeing the movement commands of the input device translated into the movement of the robotic arm. The user is thus "in the loop" as far as control and guidance of the robotic arm is concerned and can make decisions for the angle and positioning of the therapy head without the need to examine a display screen having a virtual representation of the movement of the robotic arm. The user may make adjustments to the positioning of the therapy head in all six DOF while being a user in the control loop of the robotic arm.

A visual display device may also be mounted on the robotic arm such that a user may manipulate the therapy head while visually scanning the display device. In this manner a user can evaluate sensor information and data on the display while simultaneously using the input device to guide the movement of the medical device, therapy head or robotic arm. The data provided by the sensor(s), and displayed on the screen would allow the user to manipulate the input device to maximize effectiveness and safety of the medical device or therapy head without being forced to look in several different directions to gather the information needed to guide the system.

In an alternative embodiment, the first control means may be a guide ring placed onto a patient body. In this embodiment, the guide ring provides targeting data, and there is a tracking system incorporated either into the robotic arm, or into the therapy head (or having elements in both). For illustrative purposes, the guidance system may be an optical tracking device that emits light from emitters on the robotic arm. The light is reflected off the guide ring on the patient body. The reflected light forms a pattern or orientation that optical detectors positioned about the therapy head are able to read. The optical sensors thus can determine where the center of the guide ring is, and provide movement and orientation command instructions to the robotic arm so that the robotic arm moves in such a fashion so as to keep the therapy head centered within the target ring.

The target ring is either transparent in the middle, or has an aperture. The aperture or transparent material must not significantly interfere with any energy the medical device may emit, nor with the sensors that may be incorporated into the medical device. The ring may be made of a pliable material so that when placed against the patient body, it conform to the contours of the patient, or it may be rigid so as to provide a definitive plane of reference for the user and/or therapy controller. The user of the system may manually move the target ring along the surface of the patient body while the tracking system follows the movement and angular changes in the target ring. The tracking system provides the appropriate command and control information to the robotic arm and the therapy head is moved so that the medical device, remains as much as possible, centered within the target ring, and angles so the medical device is perpendicular to the general plane of the target ring.

Alternatively the user may place the target ring onto the patient in a single place, and permit the micro controller (the second control means) to treat an area within the center of the guide ring.

The target ring may be manufactured having one side adapted for smooth gliding over the patient body. It may be treated with a silicon or polymer material to reduce friction of the device as it moves over the patient. The side facing the tracking system (facing away from the patient body) has sufficient visual cues or markers on it to produce an asymmetric reflection or refraction image. In this way the tracking system will be able to determine a direction of facing, and rotate to adapt to the rotation of the target ring so the medical device or therapy head is properly oriented at all times.

The target ring may be physically joined to the therapy head by using wires or similarly capable strain gauges around the perimeter of the therapy head and connected to the target ring. The movement of the target ring over the patient body produces strains in the wires or strain gauges that the electronic controller can detect, and correspondingly move the therapy head in response to reduce the strain. In this manner the therapy head can follow the target ring using a physical connection. Alternatively the therapy head may have a magnetic coil with the target ring having a similar magnetic field. Changes in the strength or charge of an electromagnetic field allow the system to detect the movement and direction of the target ring and compensate accordingly by moving the therapy head in response.

Alternatively, the tracking system can be made to follow a detectable path traced or imprinted onto the patient body. In this embodiment, a user or operator may set the therapy head onto the patient body, in physical contact, or in close proximity to the patient body. The tracking system thus serves as the first control means and automatically follows the path on the patient body. The second control means may be an input device a user can control to provide micro-control of the position of the medical device while the therapy head is tracing a path over the patient body. Alternatively, the electronic controller or therapy controller may have a program for moving or oscillating the therapy head or medical device. This movement or oscillating would serve as a "wobble" like effect that would sweep out an area under the patient skin that the transducer was focused on while the tracking system is operating.

Fiducials may be placed on the patient skin for the tracking system to follow. It is not necessary for a path to be drawn on the patient body for the tracking system to follow if the electronic controller has a program or designated response for tracking over a surface area defined by discrete fiducials. In this case, the first control means can be used to bring the robotic arm and therapy head into position within an area defined by fiducial markers. The second control means can then take over and move the therapy head within the fiducial markers according to its program parameters. The software program that guides the movement of the medical device or therapy head becomes the second control means. Where the surface area to be treated is large, the first and second control means may operate cooperatively simultaneously. That is the user may guide the robotic arm while the therapy program operating as the second control means handles the movement of the medical device within the defined treatment area.

Yet another embodiment would be to combine the tracking system with an input device so that a user can use the input device to manually direct the robotic arm, therapy head and medical device to follow the path traced out on the patient body. Once again the second control means may be an automated path adjustment instruction providing an artificial wobble to the movement of the therapy head as the robotic arm traces out the path on the patient body.

Still another embodiment calls for the use of a customized input device of similar design to a computer input device, but being incorporated into the robotic arm during construction. In this embodiment, the control means is integrated into the distal end of the robotic arm substantially near the therapy head. The integrated first control means utilizes technology similar to those of computer input devices such as optical tracking elements, strain gauges, force and torque converters and the like. However the input device is built having the same DOF as the arm, and it positioned for the ease of use of the user.

The second control means provides movement command and control of the medical device within the therapy head. The second control means is used where the therapy head has a micro-motor assembly, or other force generating means for the movement of the medical device within the therapy head itself. In this manner the robotic arm can be commanded to move the therapy head into a desired position or location relative to a patient body, and the second control means can be used for the precise placement of the medical device. Thus the first control means provides a "macro" level of control while the second control means provides a "micro" level of control.

Alternatively the second control means can be a software program that provides movement instructions to the micro motor assembly within the therapy head. Thus the precise placement of the medical device during a medical procedure may be left to an automated system. This enables the system to place the medical device in precise locations, for precise time intervals, in response to either pre-established parameters, or in response to real time sensor data.

In another alternative embodiment of the second control means, an automatic steering variation or "wobble" can be incorporated into the movement instructions relayed from the first control means to the robotic arm. In this manner the first control means still provides the "macro" level movement commands, but an automatic variation provides for some "micro" level of movement command that cannot be imitated or implemented through the direct translation of the movement directions received from the first control means.

In still another embodiment, the input device used as the first control means can be switched between a macro guidance mode and a micro guidance mode. A switch can be used to toggle between the modes, allowing a user to interact with a single input device and have both the first and second control means available. In operation a user can use the input device as the first control means to provide macro positioning of the robotic arm and placement of the therapy head or medical device. Once the therapy head is in the vicinity of the area to be treated, as best as can be determined by the macro level guidance, the user can toggle to a micro level of control. The input device now becomes the second control means for the fine control of the medical device within the therapy head. Alternatively, fine motor controls attached to the main force generating means used for the robotic arm can provide the micro level control while using the same force generating device. This is analogous to the coarse and fine focus found on a light microscope. The application in the motor usage of the robotic arm would be one of controlling fine mesh gears versus ordinary gears, or fine versus coarse force generating elements.

The robotic arm should also have positional or movement encoders built into it. Encoders are used to track the position of the therapy device, and the movement of each arm segment during the use of the system. Similar to robotic arms used in heavy lifting or other commercial applications, it may be preferable for the robotic arm to have a teaching mode. The teaching mode can be used by an operator to manually guide the arm through a desired set of movement operations. The electronic controller can "observe" the movement of the arm and memorize the starting position, final position and path taken between the start and final position. The motion can be memorized by the electronic controller and repeated as often as desired by recalling the movement instructions. Multiple movement paths may be stored if desired in computer memory.

In the embodiment where the input device is mounted to the arm, a slip joint may be incorporated in the arm to help isolate some amount of excess force or torque used on the input device from effecting the movement position of the robotic arm. The slip joint may be any device or joint that permits the absorption of force. For example, rotational force may be expended on the input device to cause the therapy head to change its axial rotation. If the user exerts too much rotational force, the input device may be pushed to a physical or artificial stop. At this point the excess rotational force may be spent in the slip joint. The slip joint itself may be a chamber or ring of bearings, with the input device mounted on a platform suspended within the bearing assembly. Once the input device reaches its stops, the additional force over comes a threshold force level and allows the platform to spin within the bearing ring. Thus extraneous rotational force is harmlessly expended. The slip joint necessarily has a pass-through for data information to be communicated from the input device to the electronic controller. The slip joint may also include a physical aperture serving as a pass through for any physical connection to the arm, or from the input device to the therapy head.

The slip joint may include additional axis in which forces can be absorbed so as to isolate the arm from unwanted forces. A double slip joint can be used to permit the free rotation of the first joint within a second chamber or bearing ring assembly. In this manner rotational and torque forces in multiple planes can be dampened to protect the accuracy of the robotic arm. Forces that exceed the maximum force the input device can absorb, and which are not neutralized by the slip joint, would be limited by the robotic arm. The robotic arm can sense external forces (those not originating from the instructions received from the input device) and compensate for them by applying opposite forces. This "station keeping" can be useful in tortuous environments where the user is aggressively handling the input device to try and position the therapy head properly. The optional slip joint is unnecessary where the input device is not mounted on the arm.

A therapy head is attached to the robotic arm. Within the therapy head is a medical device. The therapy head is generally located near the distal end of the robotic arm. There is no absolute requirement that the therapy head be located near the distal end. One feature of the therapy head is that it may be positioned on the robotic arm in a movable fashion so that the therapy head can traverse along the length of the robotic arm depending on the needs of the particular procedure. The therapy head may contain or comprise a variety of different components as is described in co-pending U.S. Provisional Patent Application 60/534,036, the contents of which are herein incorporated by reference.

An electronic controller is used to coordinate the functions of the various elements of the system. The electronic controller can be one or more computers, or other dedicated electronic device adapted for use with the present system. The electronic controller receives the input information from the first control means, whether it is a computer input device, guide ring or tracking system. The electronic controller then translates the input information into movement instructions for the robotic arm. A second data path may be implemented which also provides for a virtual visual object to be represented on a display device. The data streams of the movement and display data paths must properly correlate so that the movement and visual representation of the movement of the system accurately coincide.

The electronic controller must also coordinate the inputs of the second control means. If the second control means operates simultaneously with the first control means, then the electronic controller must coordinate their movements so that the medical device passes over the treatment area of the patient body in a manner in accordance with the medical procedure being performed. It is imperative the electronic controller accurately compile the movement commands of the first control means and the second control means so that there is no danger to the patient. If the second control means operates in a separate time frame from the first control means, then the electronic controller merely needs to ensure that the command and control of the medical device position is being properly controlled from the appropriate controller. Similarly, the electronic controller must ensure the safety to the patient body by preventing unauthorized or inappropriate movement of the medical device over the patient body.

The electronic controller may act as a therapy controller. If a computer is used as the electronic controller, it may have the ability to execute either preloaded software that can function as a controller for the medical device, or it may have an expansion slot such as a PCI bus interface that can accept one or more boards that operate as the therapy controller. It is advantageous but not essential for the electronic controller of the present invention to be in intimate electronic communication with the therapy controller of the medical device to ensure the movement and physical placement of the medical device and therapy head is done in accordance with the therapy procedure.

The second control means may be a physical device used to provide input, such as a secondary computer input device, or the first control means after being toggled to provide fine position control. Alternatively the second control means may be a software program to provide preprogrammed movement instructions to the medical device within the therapy head. Similarly the second control means may be a fixed or limited variable movement automatically added to the first control means movement instructions, to provide a wobble or other steady state variation to the robotic arm movement.

The medical device may be an ultrasound transducer for either diagnostic or therapeutic use. Alternatively the medical device may be a composite device of two or more types of ultrasound transducers, or a device such as described in co-pending U.S. Provisional Patent Application 60/534,034.

The medical device is secured within a therapy head. The medical device may be mounted in either a fixed position, or on a motor assembly allowing for the medical device to be moved within the therapy head. As previously described, the therapy head is in of itself, a miniature medical apparatus on the robotic arm. In a preferred embodiment, the therapy head is located substantially at the distal end of the robotic arm. The therapy head is movably positioned at the distal end of the robotic arm. Thus the therapy head may be on a movable joint allowing for the therapy head to change its orientation and/or angle with respect to the distal end of the robotic arm.

The DOF of the first control means may be separated into elements that are robotic, and elements that are manual. The robotic arm may be constructed with any number of DOF while the therapy head is manually adjusted for the remainder requirement DOF. E.g. if the robotic arm is constructed with three DOF, and the first input device is a computer input device having three DOF, then the therapy head may be mounted on a joint allowing three additional DOF that are not provided by the robotic arm. The tracking system would still follow the location of the medical device compiling both the manual and the robotic DOF elements into a single spatial location for both visual representation and medical procedure tracking purposes. Such a system may have the therapy head mounted axially to an input device, wherein the robotic arm can be adjusted through the input device while the therapy head may be simultaneously "aimed" manually.

Note that the use of a manual addition to the control means may be a component of either the first or second control means. If the therapy head has micro position motors for the movement of the medical device within the therapy head, the manual contribution to the DOF of the therapy head would be a component of the first control means. The first component in this case would be the command and control of the robotic arm. Here a user may use the therapy head itself as the input device to steer the therapy head and the robotic arm. The micro position control would remain with the therapy controller or the electronic controller and move the energy emitter within the therapy head. Alternatively if the medical device is fixed within the therapy head, then the manual contribution to the DOF would constitute the second control means while the command and control of the robotic arm would remain exclusively the first control means. Here the manual positioning takes the place of an automatic adjustment to the robotic path or artificially induced wobble.

The therapy head may also have a haptic sensor incorporated into it. The haptic sensor provides pressure feedback to the user through the first control means or through a display or alert device. The sensor measures the pressure the therapy head exerts on the patient body and provides the user with either resistance feedback, or graduated pressure information to allow the user to feel the amount of pressure the therapy head is exerting on the patient skin during a procedure. The feedback can be used to give the user sufficient tactile responsiveness to prevent the robotic arm from injuring the patient. Alternatively the robotic arm may have a safety limitation placed on the resistance feedback to prevent injury to the patient, or to prevent overly deforming the skin contour of a patient during a procedure. Specifically where the medical device is or comprises a therapy transducer for treatment of adipose tissue, it is important that the tissue volume not be overly compressed or deformed to the extent that the focal zone of the transducer no longer lays within the volume of adipose tissue. Since the tissue volume is "soft" (as opposed to muscle tissue or areas having bone or hard tissue near the surface) it is easily deformed. Thus the haptic sensor is necessarily adjusted to be responsive to even small pressures on the patient skin. This allows for a stronger resistance feedback to the user with a minimum of tissue deformation.

The haptic sensor works in combination with a load sensing device that is used to keep the therapy head in contact with the patient body. The load device can be part of the robotic arm force generating mechanism, or a separate counter balance device used to counter a portion of the therapy head weight while allowing sufficient weight to transfer through the therapy head to keep the therapy head engaged with the skin surface.

Descriptions of the system have so far focused on the first input device being positioned within close proximity to the therapy head. However the first and second control device may be positioned further away from the therapy head. For example where the robotic arm and therapy head are intended to be operated remotely, then the control means may be positioned near a remote computer with the user following a visual or virtual representation of the movement of the therapy head over the patient body. This alternative embodiment is reserved for unusual medical procedure where it is not desirable for the physician to be in close proximity to the patient body.

The moving means or motor of the articulating arm should have a rate limit such that the arm is not prone to any movements that would cause harm to the patient or operator. The movement controller thus would control the speed of both the end effector repositioning, but also the speed at which any single segment of the arm would move through space, thus avoiding or at least reducing the possibility of catching an operator or observer unaware.

The articulating arm previously described (U.S. patent application Ser. No. 10/751,344 entitled Articulating Arm for Medical Procedures) is shown in FIG. 1. The robotic arm 200 is anchored to a base 100 rolling on a plurality of castors 102 and having a brake 110. There is a handle 120 provided to facilitate the movement of the device. A computer 400 serves as an electronic controller to coordinate the therapy controller 250 and the therapy head 500. A motor 232 is used to drive the arm segments 204, 206, 208 using force generating device 234, 236, 238. Actuation of the arm segments occurs about a support member 202, and a plurality of arm joints (or other joints) 210, 212, 214, 216, 218. Encoders 222, 224, 226, 228 are used to accurately measure the position, and changes in position, of the robotic arm 200. An optional display device 242 may be mounted on the arm 200 via an adjustable connector 240 to display sensor or use data to a user standing near the therapy head 500. The therapy head 500 is connected to the robotic arm 200 via a retainer 260. The computer 400 and therapy controller 250 can work cooperatively to guide the articulating arm during a medical procedure.

Figure 2:
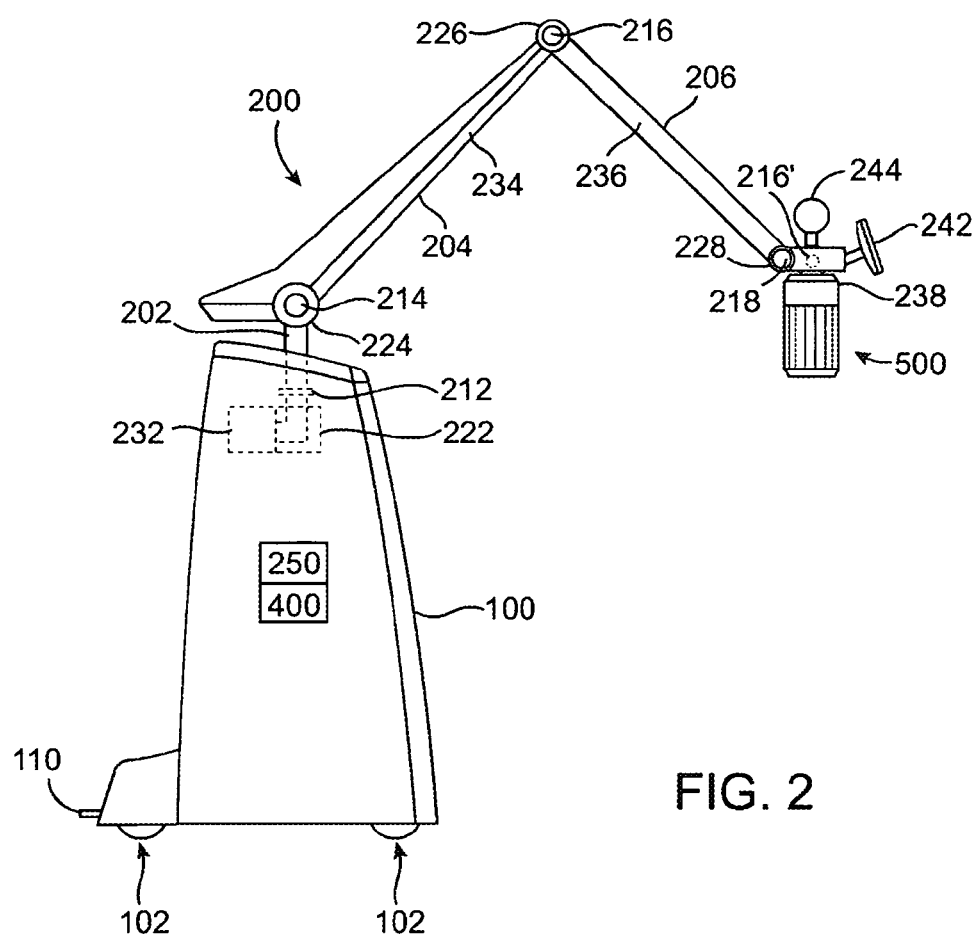
FIG. 2 illustrates a robotic arm of the present invention.

The robotic arm of the present invention is shown in FIG. 2. The principle mechanical elements are similar to those shown in FIG. 1, with the addition of an input device 244, and a slip joint 216' to separate the force and torque exerted on the tracking elements of the input device 244, from the movements of the robotic arm 200 and the therapy head 500. Input signal commands are conveyed through a communications link (not shown) to the electronic controller 400. The input signals are translated into both virtual image information and movement commands. The virtual image information may be displayed on the optional display device 242, or a fixed monitor attached to a computer work station (see FIG. 7B). The movement commands are conveyed to a motor 232, and force generating devices to cause the movement of the therapy head 500 to correspond with the virtual position and/or orientation in three-dimensional space. The use of the many encoders in the previous description are optional here, with the addition of the second level of control for user or machine "micro" level control.

Figure 3A:
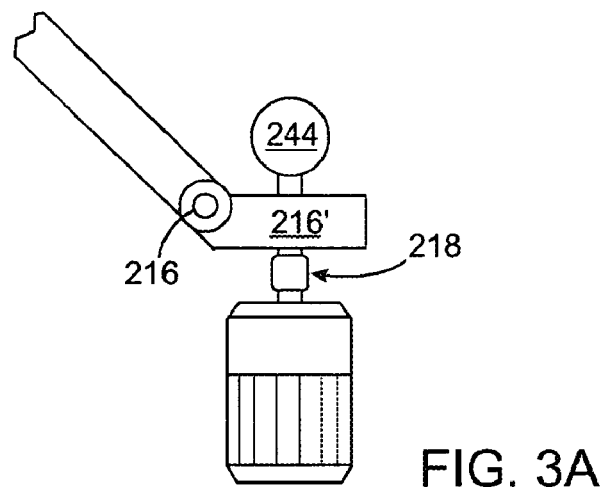
FIG. 3A illustrates an input device and a slip joint.

Various forms of input device for use in directing the position of the therapy head 500 are illustrated (FIG. 3A). In one embodiment there is a six DOF force and torque converter positioned substantially near the therapy head 500 (FIG. 3A). The input device 244 is shown being positioned directly opposite the therapy head 500 through the distal most arm segment 208 of the robotic arm 200. A distal joint 218 provides for rotational movement to the therapy head 500. The control of all the joints and force generating devices in the robotic arm are controlled by the first input device 244. The distal join 218 may be programmed into the control of the first input device, or separated out into the second control means if desired. A slip joint 216' is used to isolate the movement and torque a user conveys to the first input device 244, from influencing the position of the therapy head 500.

Figure 3B:
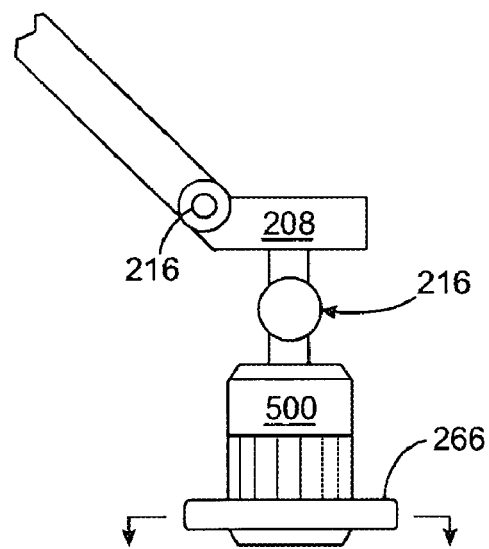
FIG. 3B illustrates a guide ring used as an input device.
Figure 3C:
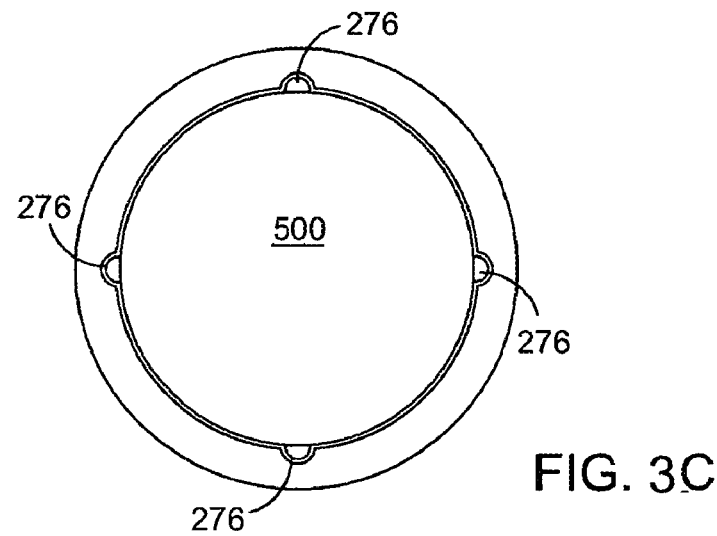
FIG. 3C illustrates a cross section of the guide ring input device.

In another embodiment there is a skirt 266 connected to the therapy head 500 via a floating fit (FIG. 3B). The skirt 266 has a plurality of contacts 276 with the therapy head 500 for determining changes in position between the therapy head 500 and the skirt 266 (FIG. 3C). These contacts can be any of a variety of position and torque detecting components. Some examples include strain gauges, potentiometers, optical encoders and the like. The skirt is not intended to have a wide range of motion, simply enough to provide force and/or torque input to the contacts when the skirt is moved, and to have a net zero input to the contacts when the skirt is in neutral position (e.g. when an operator is not exerting any force on the skirt). In this embodiment is not necessary to include the buffer joint 216' and it is preferably omitted.

Figure 4A:
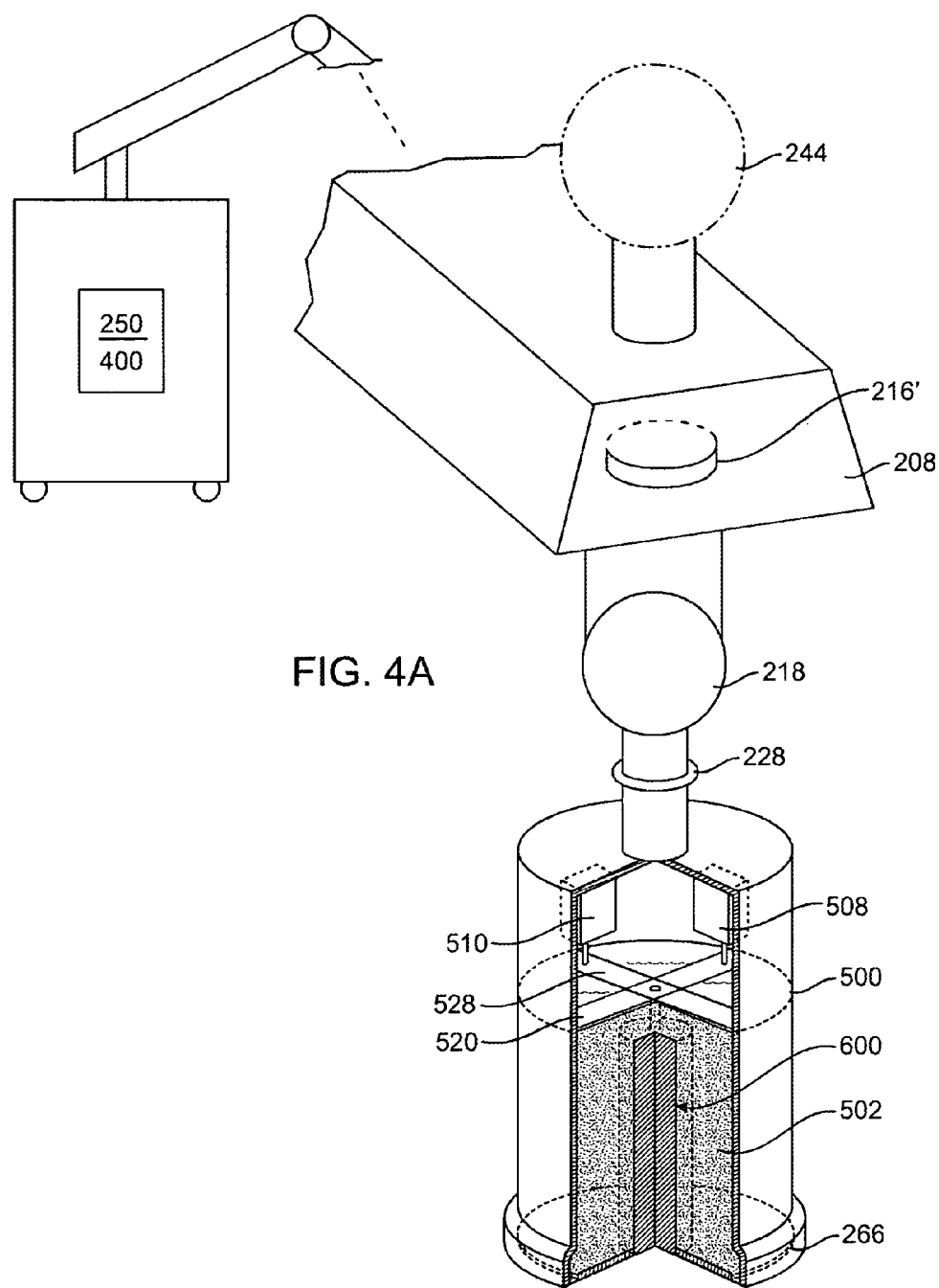
FIG. 4A shows a prospective view of the therapy head and arm.
Figure 4B:
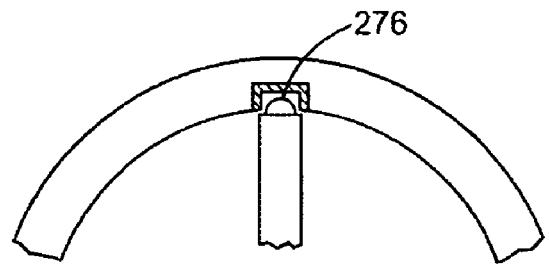
FIG. 4B-D show alternative embodiments of the input device detectors.
Figure 4C:
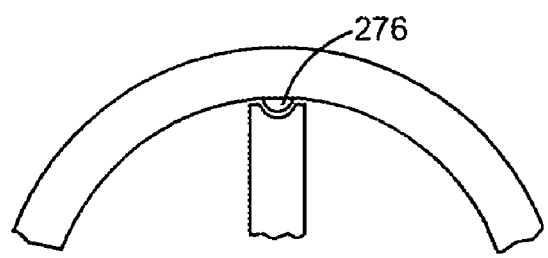
Figure 4D:
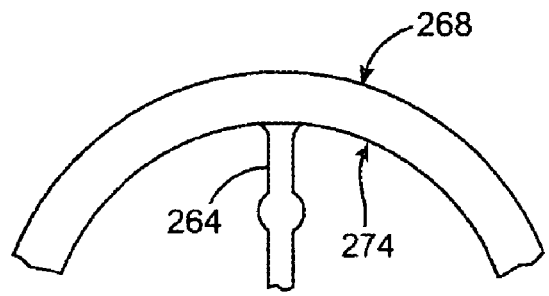
Figure 5A:
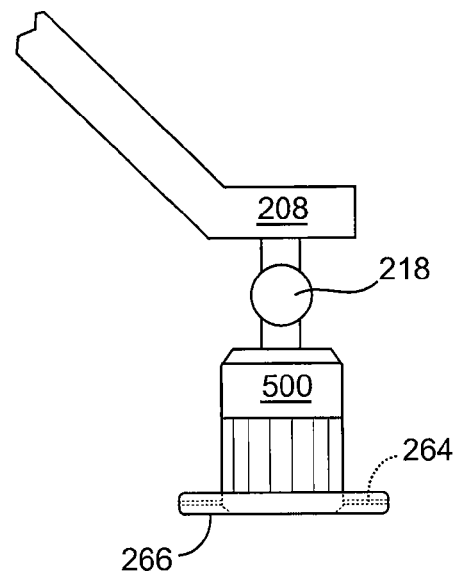
FIGS. 5A-B show a guide ring using strain gauges.
Figure 5B:
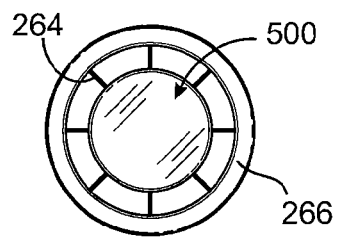

The skirt 266 can be maneuvered manually and is preferably located near the contact surface of the therapy head. However it is not required that the skirt itself be in contact with the patient skin surface. The skirt 266 can have a series of potentiometers to act as sensor contacts for determining movement between the skirt and the therapy head (FIG. 4B-C) or it may use a plurality of strain gauges 264 (FIG. 4D, 5A-B). Where a plurality of strain gauges are used, the skirt is preferably positioned to be in contact with the patient body. A user can move the skirt on the surface of the patient body to match the contours of the skin surface. The strain gauges provide the necessary directional information to the electronic controller and thus direct the movement of the robotic arm. It will be appreciated there must be sufficient contact sensors to establish a true vector of movement in three dimensional space, regardless of the type of contact used.

Figure 6:
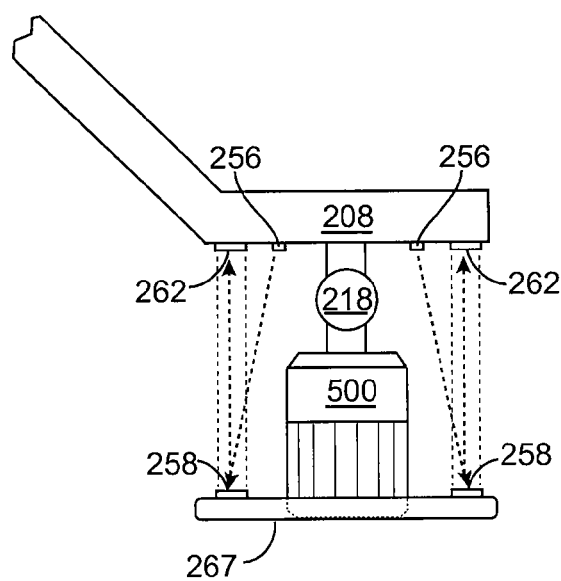
FIG. 6 Shows a free floating guide ring and an optical tracking system.

In another embodiment, a free floating guide ring 267 having an asymmetric optical reflector 258 can be used as the first control means (FIG. 6). In this embodiment, the robotic arm includes optical emitters 256 and optical detectors 262 at the distal end of the robotic arm 208. The emitters 256 transmit light toward the guide ring 267 which is placed on the patient body. The reflection is received by the detectors 262. The reflectors 258 may be arranged in an asymmetric pattern such that the orientation of the guide ring and the therapy head can easily be determined. The detectors must have sufficient sensitivity to detect movement of the guide ring and determine both the vertical and horizontal displacement of the guide ring from frame to frame. The detector data is relayed to the electronic controller. The electronic controller determines the displacement and sends the appropriate movement commands to the robotic arm so the arm can reposition the therapy head. In this manner the therapy head is constantly kept in the central portion of the guide ring. As the guide ring 267 is moved by an operator (not shown) the motors in the robotic arm keep the therapy head centered in the guide ring. If the guide ring changes its angle of contact relative to the starting plane of orientation, the distal joint 218 is also robotically controlled, thus as the optical detectors determine a change in planar orientation, the therapy head can be moved to compensate.

FIG. 4 provides a view of the first and second control means relative to each other. The first control means for guiding and directing the movement of the robotic arm 200 is shown either as a force and torque converter type of input device 244 or as a direct manipulation skirt 266 having a floating interference connection to the therapy head 500. Additional devices as previously described may be used as the first control means input device. The first control means provides the macro level of control for properly positioning the therapy head. The distal joint 218 may be part of the actuated elements of the robotic arm and controlled through the first input device 244, 266, or it may be made as part of the micro level of control and thus controlled through the second control means. The therapy head 500 is shown with a fluid 502 surrounding the energy applicator 600, and a pair of motors 508, 510 for micro positioning of the energy applicator. The motors 508, 510 are linked to the energy applicator through a pair of linkages 520, 528.

The first input means, if separated from the therapy head, is isolated from the therapy head by an isolation buffer joint 216'. In operation the slip joint 216' provides a limited resistance so force and torque exerted by a user is first conveyed to the input device 244. However if the user exerts an excessive amount of force or torque, the slip joint 216' provides slippage so that excess energy does not influence the direction and control of the robotic arm itself. In this way the robotic arm can be truly steered with a user's direct input through the input device 244, without throwing off the guidance due to excessive force and torque as may occasionally come about through a users carelessness, or unfamiliarity with the apparatus. In this manner, a physician can grasp the first input device 244 and manipulate it without putting unwanted force and torque directly on the robotic arm 200. Once the therapy head 500 has been properly positioned, the therapy device 600 is manipulated within the therapy head 500 by a second control means.

The second control means may be a pair of micro-positioning motors 508, 510 mounted within the therapy head. Control of the micro-positioning motors 508, 510 comes from either the therapy controller 250 or the computer 400. The therapy controller 250 may be incorporated into the computer 400. The therapy controller 250 may guide the therapy device 600 by electronically controlling the micro-positioning motors 508, 510. This electronic control may be in the form of software instructions provided by accessing a library of programmed movement instructions, or it may provide electronic control based on a secondary input device, which is controlled in real time by a user.

The user may operate the medical arm directly (FIG. 7A) when the input device 244 is positioned in close proximity to the therapy head 500. The operator can see any diagnostic or parameter data on the display 242 while observing the patient P, therapy head 500 and the input device 244 simultaneously. This provides for an optimum level of control for a physician. The weight of the therapy head is supported by the robotic arm 200. As the user maneuvers the input device, electronic signals are relayed to, and processed by the electronic controller 400. As the macro positioning occurs, the second control device handles the micro positioning within the therapy head. The second control device may be the therapy controller 250, or alternatively a user controlled input device similar to the first control device. Once again the second control device preferably has the same DOF as the therapy device moving within the therapy head. A slip joint 216' is used to isolate the arm and therapy head from direct force from the user.

Figure 7B:
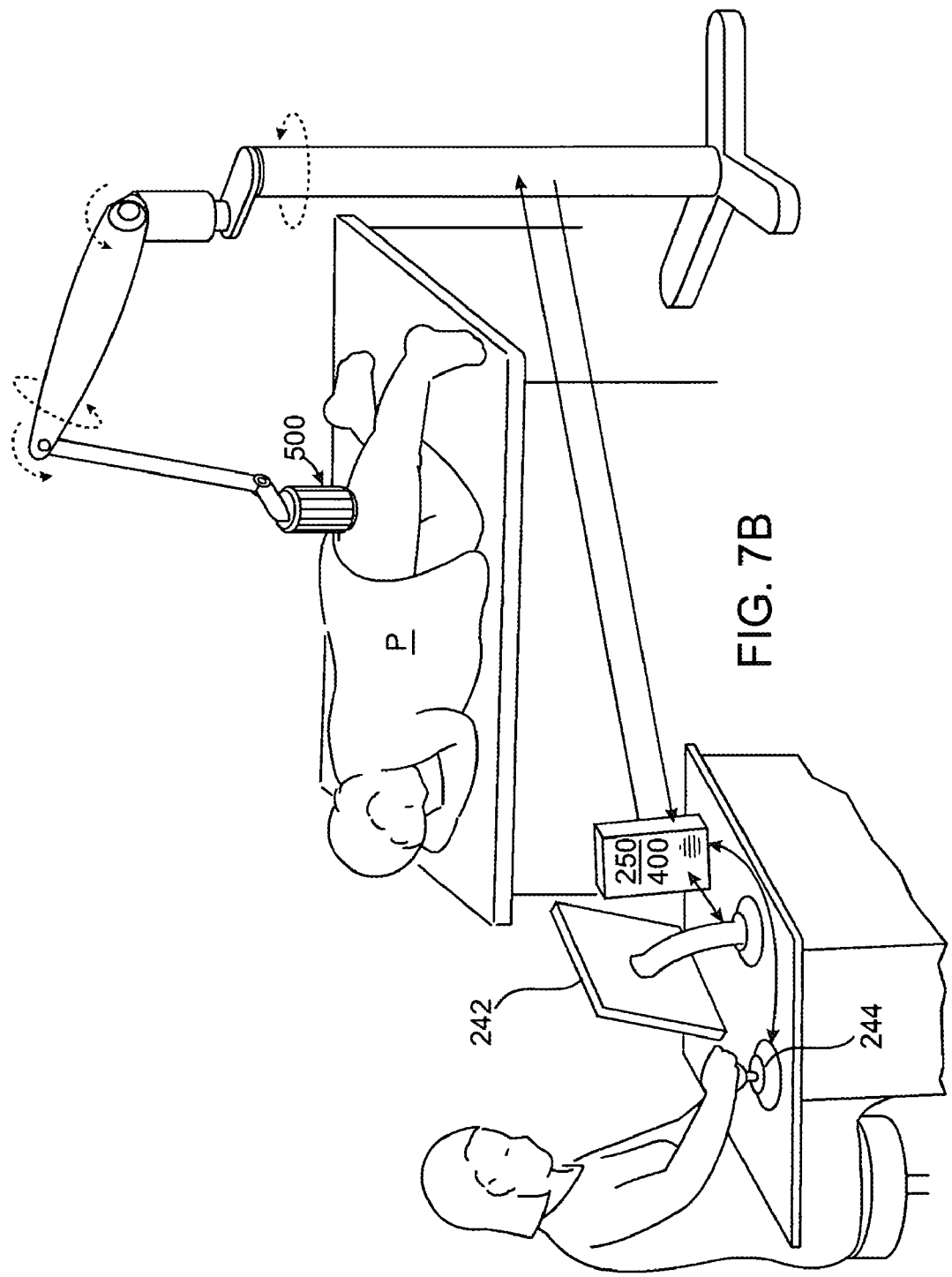

Alternatively the first control means may be attached to a computer workstation 400 incorporating the therapy controller 250. The user may operate the apparatus remotely from the patient (FIG. 7B). The apparatus is controlled in the same manner as above. Desirably a sensitive haptic feedback system is integrated into the therapy head to provide the user with tactile feedback during a treatment. The haptic sensor should include a pressure limit sensor so the robotic arm does not apply excess pressure and cause injury to the patient.

In both the proceeding examples, the second control means may be the same as the first control means. Although a second input device may be provided for the fine manipulation of the therapy device, most users preference for one hand makes it more ergonomic, and more efficient for the first input device to have a switch allowing a user to toggle back and forth between a macro level of guidance and a micro level of guidance. As described previously, the therapy controller may maintain a volumetric map of the tissue volume to be treated and can put the therapy device into a stand by mode when the therapy device is over an area previously treated. This safety allows a user the freedom and ease of switching back and forth between macro and micro level of control without worrying about the patient being over treated.

Figure 7C:
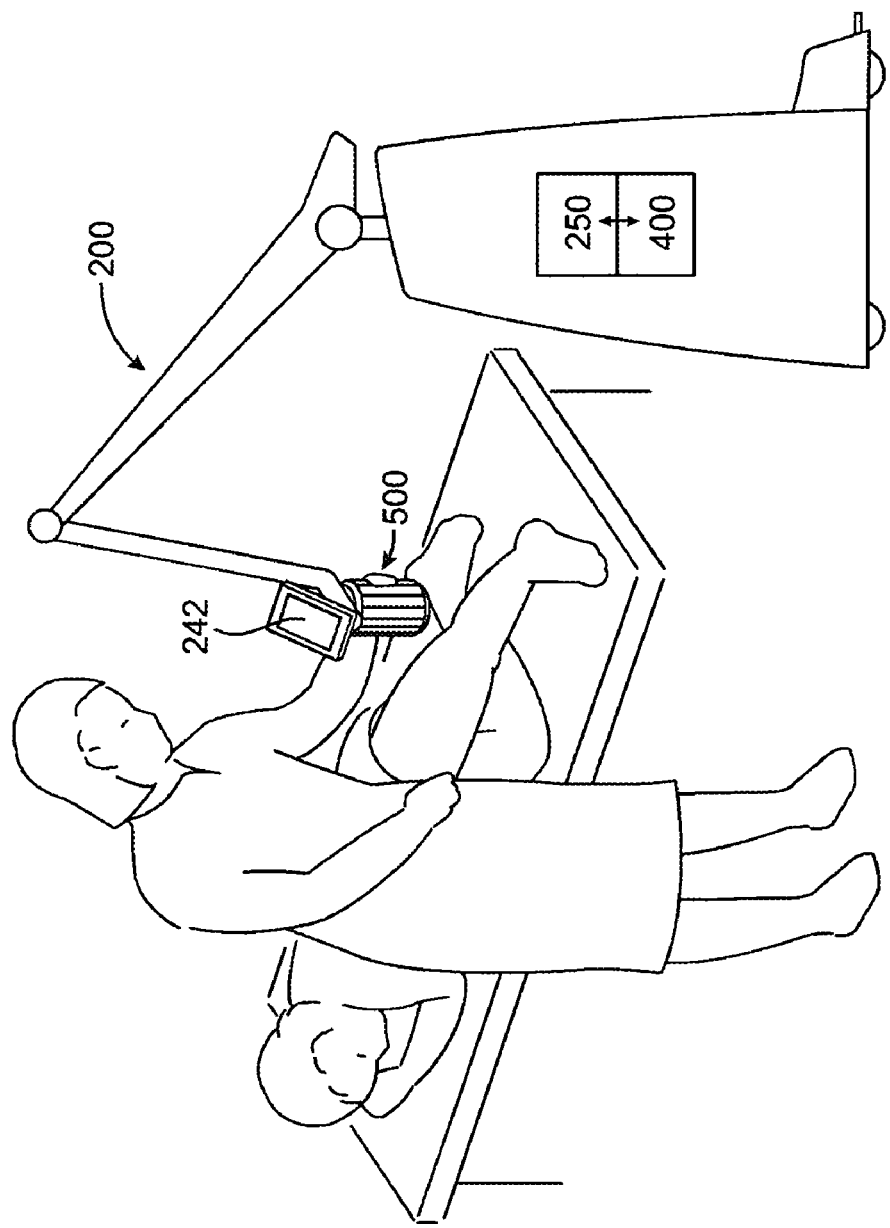

The user may grasp the therapy head 500 directly and use it as the input device to guide the robotic arm. The therapy head can be the input device and so serve as the first control means for controlling the movement of the robotic arm 200 (FIG. 7C). In this embodiment the display 242 is positioned on top of the robotic arm 200 so as to not interfere with the manual manipulation of the therapy head. An input device similar to those previously described 244 may be used in this embodiment where the user may use either the therapy head 500 or a dedicated input device 244.

Figure 8A:
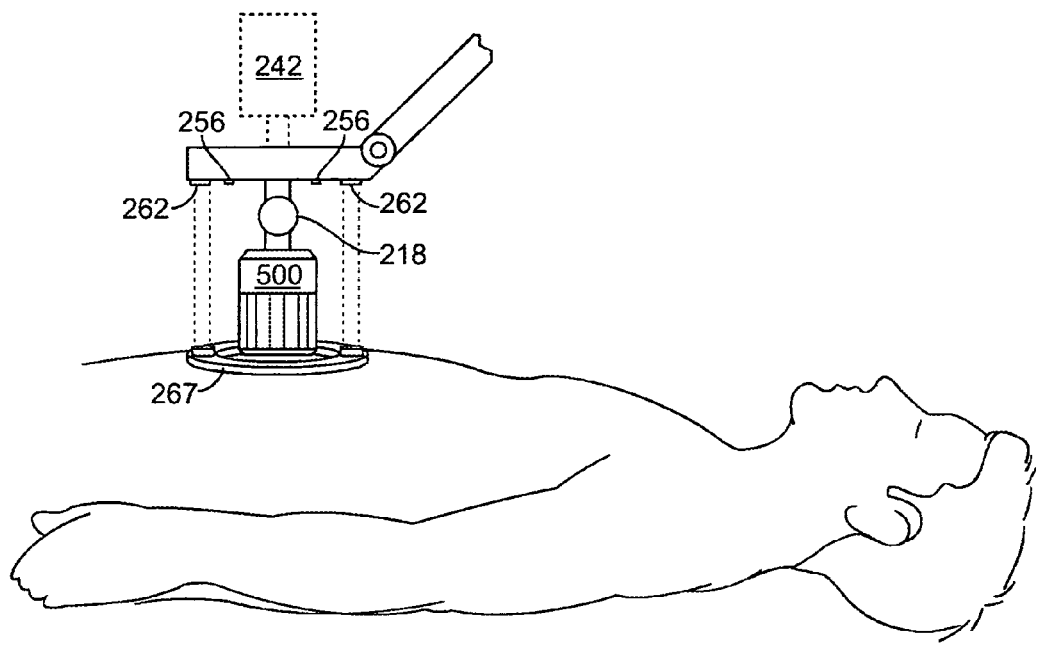
FIGS. 8A-C illustrate the guide device in operation in a medical procedure.
Figure 8B:
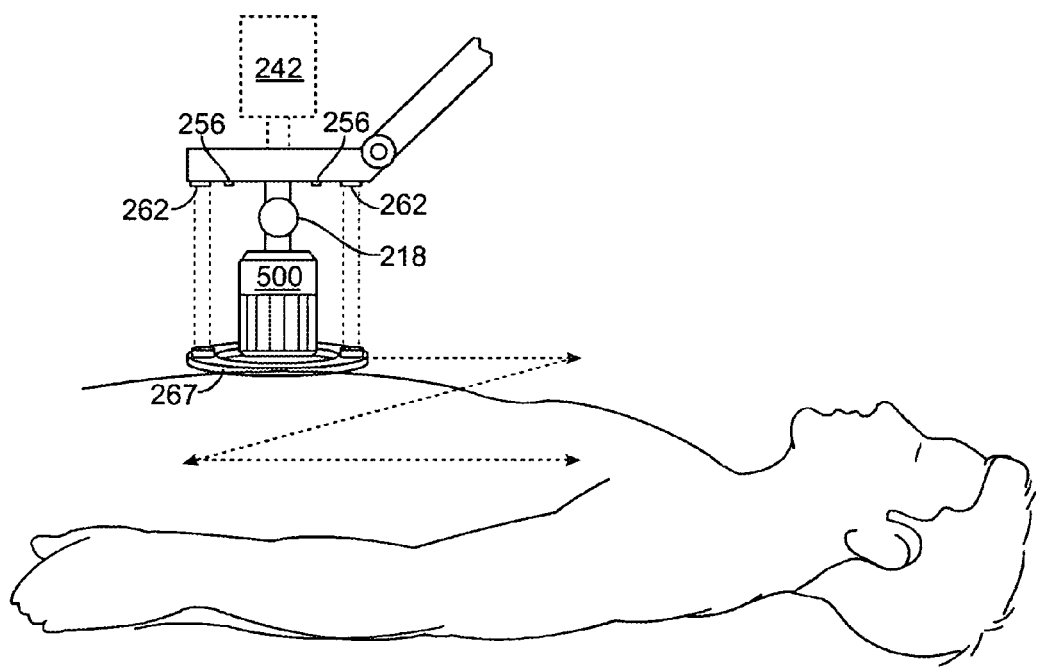

In another embodiment, a guide ring 267 is placed directly on the patient body. The guide ring 267 is not physically connected to the therapy head 500 or the robotic arm 200. A tracking system incorporated into the distal end of the robotic arm 208 is used to monitor the placement and orientation of the guide ring 267. The tracking system acts as the macro level input device and responds to movements of the guide ring as the physician moves the guide ring over the patient. Each movement or change in orientation provides the tracking system with the necessary vector information to move the robotic arm, and orient the therapy head to match the position of the guide ring. Thus as a user moves the guide ring, the therapy head follows the ring and maintains its position in the center of the ring. The guide ring may be transparent or semi-transparent to assist the user in seeing the patient skin surface as well as any fiducials that are placed on the patient body to mark the outlines of the volume to be treated. Grid lines or other optically detectable patterns may be used to provide an optical tracking system with a method of orienting the alignment of the guide ring and therapy head. The tracking system and guide ring have sufficient DOF so the arm can be made to follow the contours of the patient body as the guide ring is moved from the initial plane of treatment, to a different plane during treatment (FIG. 8A-B).

Figure 8C:
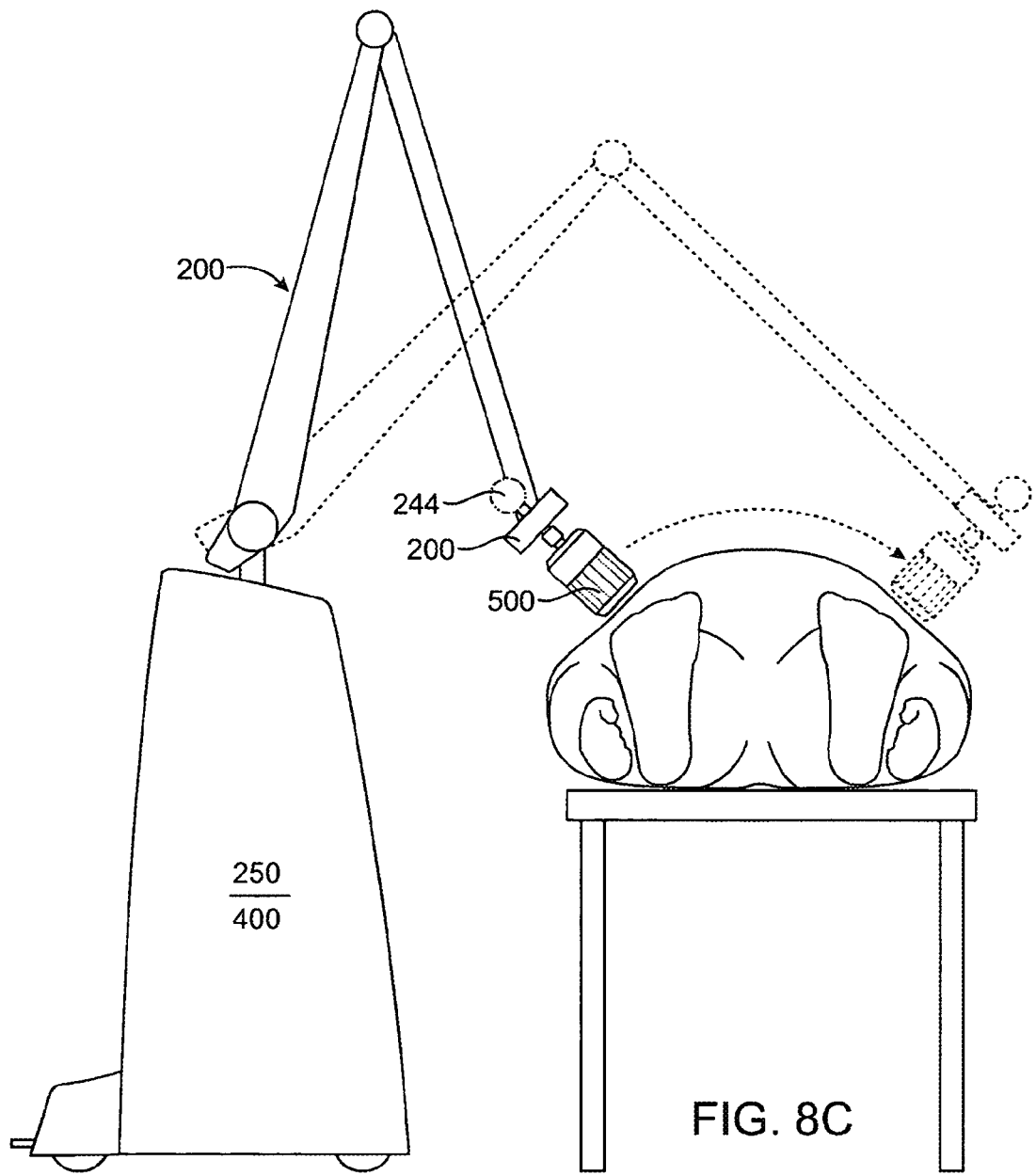

The first input means may be a visual trail drawn on the patient body, or drawn with an electronic pen that the robotic arm is able to track. The first input device in this embodiment is similar to a computer tablet and stylus system where the patient skin surface acts as the tablet, and the therapy head acts as the stylus. The patient may have an area of skin outlined for treatment and the user manually maneuvers the therapy head within the outlined area, and the therapy head leaves behind a biocompatible marker trail similar to lines drawn on a tablet with a stylus. The user is able to see what areas have been treated directly on the patient. The therapy controller handles the micro positioning of the therapy device within the therapy head and also updates the volumetric map of the treatment session. The user can refer to a display device to check the progress of the treatment and evaluate the visual trail on the patient, and the volumetric map in the computer (FIG. 8C).

Figure 9A:
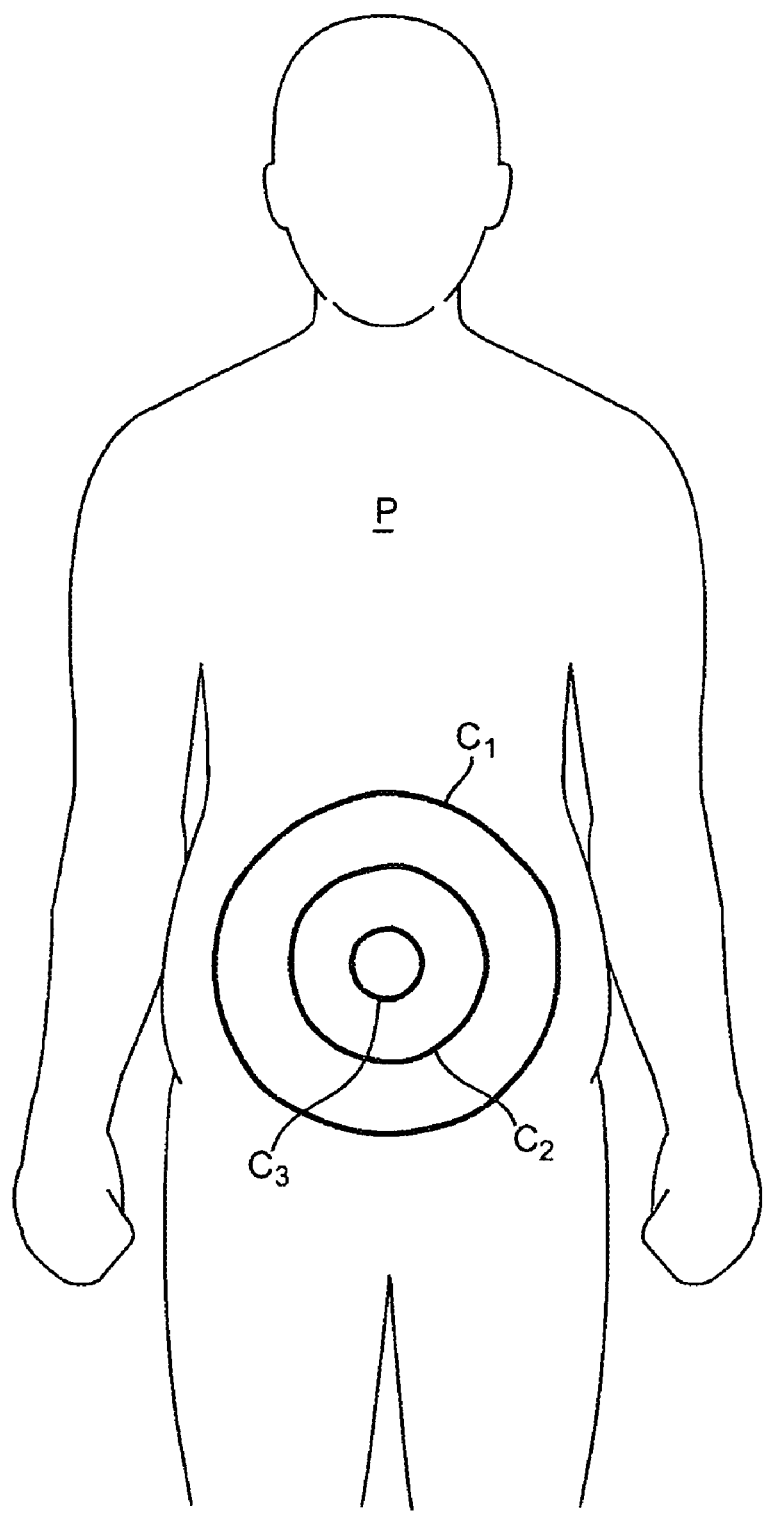
FIG. 9A-C show the placement of the contour and grid lines on a patient body.
Figure 9B:
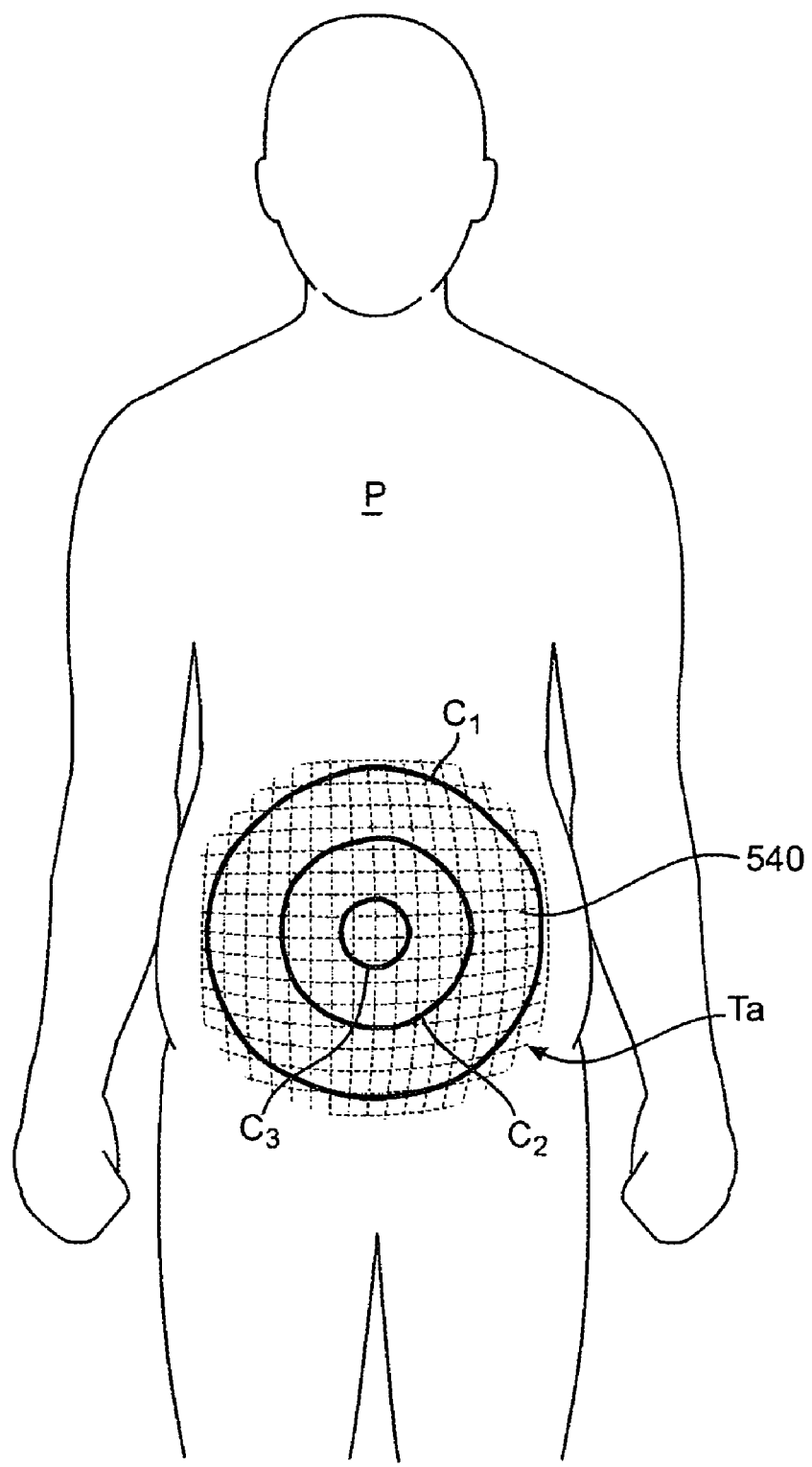
Figure 9C:
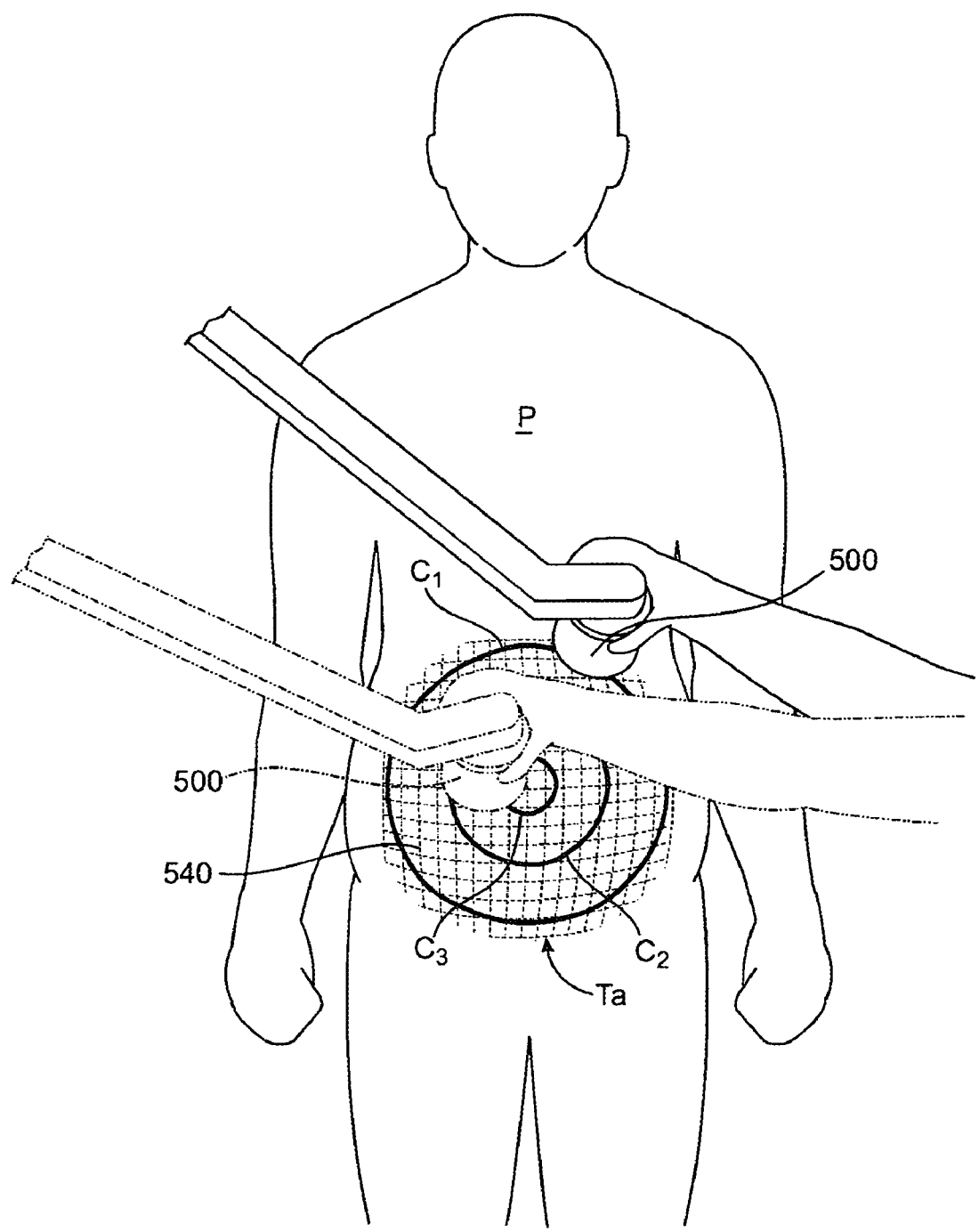

In operation, a user can determine the treatment area for ultrasound therapy in the same fashion as in a liposuction procedure. The user can use the look and feel of the patient to draw one or more contour lines $C_{1-3}$ on the skin of the patient. Contour lines provide a visual boundary a user can follow. Once the user has drawn the contour lines on the patient, a treatment grid is overlaid on the patient skin (FIG. 9B). The grid may be drawn using a device, template, stencil or freehand. The grid provides the user with an easy way to follow the progress of the ultrasound therapy.

Once the gridlines are in place, a user can utilize the two-step control system of the present disclosure to guide a therapy ultrasound device across the patient and perform noninvasive tissue necrosis. The grid lines provide an organized manner in which the user can move the therapy head over the patient body. Preferably the therapy controller 250 and/or electronic controller 400 will track and determine the volume of tissue that is treated. The user can rely on the data provided to him through the display device 242, and the visual information presented before him on the patient's skin. The user may use a fiducial marker to "check off" grid squares he has already treated, or he may rely on the electronic controller to mark off grid squares through the display device, or through the depositing of a fiducial in each grid square as the therapy head 500 advances over the patient body.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

What is claimed is:

1. An apparatus for guiding the movement of an energy emitter over a patient body, the apparatus comprising:
   a movable therapy head having at least one energy emitter;
   a guide ring adapted to be placed on and moved over the patient body, wherein the guide ring is not fixed to the therapy head; and
   a tracking system for following the movement of the guide ring and keeping energy from the energy emitter of the therapy head substantially centered within the guide ring,
   wherein the tracking system causes the therapy head to follow the guide ring as the guide ring is moved over the patient body, and
   wherein the tracking system comprises:
      at least one optical emitter coupled to the therapy head;
      a plurality of optical reflectors on the guide ring; and
      a plurality of optical detectors coupled to the therapy head,
   wherein said at least one optical emitter transmits light toward said guide ring such that light is reflected or scattered back from the guide ring toward said detectors in a pattern that allows said tracking system to coordinate the center of the ring with a position of said movable therapy head.

2. The apparatus of claim 1, wherein said guide ring comprises a plurality of fiducials.

3. The apparatus of claim 1, further comprising a robotic arm configured to support the therapy head.

4. The apparatus of claim 1, wherein said tracking system further comprises a target window having one or more targeting grids, and is programmed to maintain said therapy head within said guide ring.

5. The apparatus of claim 1, wherein the movable therapy head has a haptic sensor and a movement limiter to prevent the therapy head from being depressed below the plane of a guide ring.

6. The apparatus of claim 1, wherein said energy emitter comprises a high intensity focus ultrasound transducer.

7. The apparatus of claim 1, wherein the energy emitter further comprises at least one sensor.

8. The apparatus of claim 1, further comprising a robotic arm.

9. The apparatus of claim 7, wherein the sensor comprises a diagnostic ultrasound transducer or an A-line transducer.

10. The apparatus of claim 1, wherein said therapy head further comprises at least one sensor.

11. The apparatus of claim 10, wherein the sensor comprises a haptic sensor.

12. The apparatus of claim 10, wherein the sensor provides feedback information to a user.

13. The apparatus of claim 1, further comprising an electronic controller for coordinating movement of the movable therapy head and the tracking system.

\* \* \* \* \*

UNITED STATES PATENT AND TRADEMARK OFFICE
CERTIFICATE OF CORRECTION

PATENT NO. : 8,337,407 B2
APPLICATION NO. : 11/027498
DATED : December 25, 2012
INVENTOR(S) : Jens U. Quistgaard et al.

Page 1 of 2

It is certified that error appears in the above-identified patent and that said Letters Patent is hereby corrected as shown below:

In the Specification:

At column 1, line number 23, change "are" to --is-- and at line number 57 change "know" to --knows--.

At column 2, line number 48, after "of" delete ";".

At column 3, line number 50, change "FIG." to --FIGS.-- and at line number 53, change "Shows" to --shows-- and at line number 55, change "illustrates" to --illustrate-- and at line number 59, change "FIG." to --FIGS.--.

At column 4, line number 33, change "principle" to --principal-- and at line number 41, change "of;" to --of,--.

At column 6, line number 59, change "is" to --are--.

At column 10, line number 39, change "over comes" to --overcomes-- and at line number 48, change "axis" to --axes--.

At column 13, line number 53, change "principle" to --principal--.

Signed and Sealed this
Nineteenth Day of March, 2013

Teresa Stanek Rea
*Acting Director of the United States Patent and Trademark Office*

CERTIFICATE OF CORRECTION (continued)
U.S. Pat. No. 8,337,407 B2

At column 14, line number 1, change "are" to --is-- and at line number 13, change "are" to --is-- and at line number 14, change "join" to --joint-- and at line number 31, after "embodiment", insert --it--.

At column 15, line number 28, change "is" to --are--.

At column 16, line number 17, change "users" to --users'--.